(12) United States Patent
Possanzini et al.

(10) Patent No.: US 10,184,996 B2
(45) Date of Patent: Jan. 22, 2019

(54) MAGNETIC RESONANCE IMAGING SUBJECT SUPPORT

(71) Applicant: KONINKLIJKE PHILIPS N.V., Eindhoven (NL)

(72) Inventors: Cecilia Possanzini, Eindhoven (NL); Christoph Leussler, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 484 days.

(21) Appl. No.: 14/898,292

(22) PCT Filed: Jun. 17, 2014

(86) PCT No.: PCT/EP2014/062607
§ 371 (c)(1),
(2) Date: Dec. 14, 2015

(87) PCT Pub. No.: WO2014/202552
PCT Pub. Date: Dec. 24, 2014

(65) Prior Publication Data
US 2016/0139218 A1    May 19, 2016

(30) Foreign Application Priority Data

Jun. 17, 2013    (EP) .................................... 13172207

(51) Int. Cl.
| G01V 3/00 | (2006.01) |
| G01R 33/30 | (2006.01) |
| A61B 5/055 | (2006.01) |
| G01R 33/34 | (2006.01) |
| G01R 33/36 | (2006.01) |
| G01R 33/28 | (2006.01) |

(52) U.S. Cl.
CPC ............ *G01R 33/30* (2013.01); *A61B 5/0555* (2013.01); *G01R 33/288* (2013.01); *G01R 33/3403* (2013.01); *G01R 33/3614* (2013.01); *G01R 33/3621* (2013.01); *G01R 33/34046* (2013.01)

(58) Field of Classification Search
CPC ..................................... A61B 5/0555
USPC ........................ 324/322, 318, 314
See application file for complete search history.

(56) References Cited

U.S. PATENT DOCUMENTS

| 7,570,056 B2 | 8/2009 | Nakabayashi |
| 7,602,186 B2 | 10/2009 | Hoogeveen |
| 7,719,271 B2 | 5/2010 | Ohsawa |
| 7,728,592 B2 | 6/2010 | Ma |
| 7,920,910 B2 | 4/2011 | Calderon |

(Continued)

FOREIGN PATENT DOCUMENTS

| EP | 2184615 A1 | 12/2010 |
| JP | 62119907 A | 6/1987 |

(Continued)

*Primary Examiner* — Louis Arana (57) ABSTRACT

The invention provides for a subject support assembly (125) for a magnetic resonance imaging system (100, 200, 300, 400, 500). The subject support is operable for supporting a subject (118) within an imaging zone (108) of a magnet (104) of the magnetic resonance imaging system. The subject support is operable for supporting at least one radio frequency amplifier (124, 124', 124") outside of the imaging zone. The subject support is operable for supplying DC electrical power to the at least one radio frequency amplifier.

20 Claims, 7 Drawing Sheets

(56) References Cited

U.S. PATENT DOCUMENTS

| | | |
|---|---|---|
| 2005/0275403 A1 | 12/2005 | Pinkerton et al. |
| 2007/0164746 A1 | 7/2007 | Jevtic et al. |
| 2008/0191696 A1 | 8/2008 | Van Der Burgt |
| 2008/0211495 A1 | 9/2008 | Stechner |
| 2009/0222987 A1 | 9/2009 | He et al. |
| 2010/0031443 A1 | 2/2010 | Georgiev |
| 2010/0315085 A1 | 12/2010 | Brown |
| 2013/0024956 A1 | 1/2013 | Bedian |
| 2013/0249560 A1 | 9/2013 | Okamoto et al. |
| 2014/0218030 A1* | 8/2014 | Harvey ............... G01R 33/30 324/309 |
| 2014/0336500 A1* | 11/2014 | Katsunuma ......... A61B 5/0555 600/415 |
| 2016/0061916 A1* | 3/2016 | Duensing ........ G01R 33/34007 324/309 |
| 2016/0077175 A1* | 3/2016 | Mori ............... G01R 33/3692 324/321 |

FOREIGN PATENT DOCUMENTS

| | | |
|---|---|---|
| JP | 20050270261 | 10/2005 |
| JP | 200800484 A | 1/2008 |
| WO | 2007066250 A1 | 6/2007 |
| WO | 2010076682 A1 | 7/2010 |
| WO | 2012161101 A1 | 11/2012 |

* cited by examiner

MAGNETIC RESONANCE IMAGING SUBJECT SUPPORT

CROSS REFERENCE TO RELATED APPLICATIONS

This application is a U.S. national phase application of International Application No. PCT/EP2014/062607, filed on Jun. 17, 2014, which claims the benefit of EP Application Serial No. 13172207.6 filed on Jun. 17, 2013 and is incorporated herein by reference.

TECHNICAL FIELD

The invention relates to magnetic resonance imaging, in particular to the radio frequency generators used for exciting the NMR resonance.

BACKGROUND OF THE INVENTION

A magnetic field is used in Magnetic Resonance Imaging to align the nuclear spins of atoms as part of the procedure for producing images within the body of a patient. This magnetic field is referred to as the B0 field. During an MRI scan, Radio Frequency (RF) pulses generated by a transmitter or amplifier and an antenna cause perturbations to the local magnetic field and can be used to manipulate the orientation of the nuclear spins relative to the B0 field. RF signals emitted by the nuclear spins are detected by a receiver coil, and these RF signals are used to construct the MRI images.

U.S. Pat. No. 7,570,056 B2 discloses a top board for placing a subject upon in an MRI system. The upper surface of the top board functions has a coil support. The coil support comprises a port configure to electrically connect the radio frequency coil to a signal cable. The top board further has a support member which includes a guide groove for permitting the port to slide. The US-patent application U.S. 2013/0249560 which is a continuation of the international application PCT/JP2012/062715 mentions n MRI apparatus which has a system connector mounted on the patient table. A local coil ha a coil connector to mate with the system connector the connect the local coil. The local coil of the known MRI apparatus has a pre-amplifier on-board. Further a transmitter is provided beyond the coil connector by remote signal lines.

SUMMARY OF THE INVENTION

The invention provides for a subject support assembly and a magnetic resonance imaging system in the independent claims. Embodiments are given in the dependent claims.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins by the antenna of a Magnetic resonance apparatus during a magnetic resonance imaging scan. Magnetic resonance data is an example of medical image data. A Magnetic Resonance Imaging (MRI) image is defined herein as being the reconstructed two or three dimensional visualization of anatomic data contained within the magnetic resonance imaging data. This visualization can be performed using a computer.

In one aspect the invention provides for a subject support assembly for a magnetic resonance imaging system. The subject support is operable for supporting a subject within the imaging zone of a magnet of the magnetic resonance imaging system. In some embodiments the subject support may be separate from the magnetic resonance imaging system and may be locked into place or moved into position for use. In other embodiments the subject support assembly is incorporated to or is integrated into the magnetic resonance imaging system.

The subject support is operable for supporting at least one radio-frequency amplifier outside of the imaging zone. A radio-frequency amplifier as used herein encompasses an electronic apparatus capable of generating radio-frequency signals and for driving an antenna or coil system used to excite NMR or MRI resonances within a subject. The subject support is operable for supplying DC electrical power to the at least one radio-frequency amplifier. It may be beneficial for the radio-frequency amplifier to be outside of the imaging zone because this means that the radio-frequency amplifier may have a reduced effect on or may not disturb the imaging zone. An imaging zone as used herein is a region with a sufficiently high magnetic field and uniform enough magnetic field for performing magnetic resonance imaging. Having the radio-frequency amplifier attached or mounted to the subject support may be beneficial because the radio-frequency amplifier is on one hand close to the antenna or coil so the losses on the transmission line between the radio-frequency amplifier and the coil or antenna is reduced. Having the radio-frequency amplifier integrated into the subject support may also be beneficial because this may help organize or eliminate the problem of cables causing problems for the magnetic resonance imaging system. For instance the DC current used to supply the radio-frequency amplifier may have an effect on the magnet field of the magnetic resonance imaging system. By having it integrated into the table the cables may be routed in a fixed or even in a beneficial way to reduce their effect on the magnetic field in the imaging zone.

In another embodiment the subject support is operable for detachably receiving the at least one radio-frequency amplifier. The term 'detachably receiving' as used herein means that the radio-frequency amplifier may be easily attached or removed from the subject support. In various embodiments there may be one such radio-frequency amplifier or it may be that a number of radio-frequency amplifiers can all be mounted onto the same subject support. Depending upon the use of the magnetic resonance imaging system it may also be beneficial to switch around or move the position of the at least one radio-frequency amplifier. There may be multiple positions where a particular radio-frequency amplifier can be attached to the subject support.

The subject support comprises a first DC electrical connector. The at least one radio-frequency amplifier comprises a second DC electrical connector. The first DC electrical connector is operable for forming an electrical connection with the second DC electrical connector. The subject support is operable for supplying DC electrical power to the at least one radio-frequency amplifier when the first DC electrical connector is connected to the second DC electrical connector. Using the DC electrical connectors in the subject support may make it easier to build a subject support which can take multiple radio-frequency amplifiers and also for moving radio-frequency amplifiers to different positions for customization during a magnetic resonance imaging procedure.

For instance there may be multiple first DC electrical connectors integrated into the subject support and the amplifier can be moved around as needed. It may also be the case that more than one amplifier can be used when there are multiple DC electrical connectors.

In another embodiment the subject support comprises a first coolant connector. A coolant as used herein is a fluid or air which has been chilled and is operable for removing heat at least from the radio-frequency amplifier that it is connected to. The at least one radio-frequency amplifier comprises a second coolant connector. The first coolant connector is operable for forming a connection with the second coolant connector. The subject support is operable to supply coolant to the at least one radio-frequency amplifier and the first coolant connector is connected with the second coolant connector. The use of connectors may make it easy to move the at least one radio-frequency amplifier to different locations if there are multiple connectors integrated into the subject support.

The subject support further comprises a sensor operable for determining if the at least one radio-frequency generator is connected to the subject support. This embodiment may be beneficial because the sensor can be networked or connected to the controller of the magnetic resonance imaging system and this can be used to determine if the radio-frequency generators on the subject support are properly connected or not. This may be important or assist in making the system safer. For instance the DC electrical power could be deactivated to particular connectors when there is no radio-frequency generator detected at a particular location.

In another embodiment the subject support comprises a first fiber optic connector. The at least one radio-frequency amplifier comprises a second fiber optic connector. The first fiber optic connector is operable for forming a connection with the second fiber optic connector. The subject support is any one of the following: operable to transmit radio-frequency control signals to the at least one radio-frequency amplifier; receive data from the at least one radio-frequency amplifier and combinations thereof. This embodiment may be beneficial because the exchange of data between the magnetic resonance imaging system's controller or computer and the at least one radio-frequency amplifier may be done using optical transmissions. The magnetic resonance imaging system operates in a high magnetic field and also with a lot of radio-frequency interference. The use of the fiber optics may result in improved control of the at least one radio-frequency amplifier.

In another embodiment the subject support comprises the at least one radio-frequency amplifier.

In another embodiment the at least one radio-frequency amplifier is incorporated into the subject support. In this embodiment the at least one radio-frequency amplifier is mounted or incorporated into the subject support such that it is not easy to detach it. This embodiment may be beneficial when a more or less permanent position of the amplifier in the subject support is desired.

When the radio-frequency amplifier is incorporated into the subject support the use of fiber optic control of the at least one radio-frequency amplifier, the cooling of the radio-frequency amplifier using a coolant may also be used.

In another embodiment the at least one radio-frequency amplifier comprises a DC electrical power storage device operable for powering the generation of pulsed radio-frequency pulses at the at least one radio-frequency amplifier. A DC electrical power storage device may be, but is not limited to: a battery, a capacitor, and combinations thereof. The radio-frequency amplifier is in this embodiment operable for supplying DC electrical power. For pulsed magnetic resonance imaging the energy required can be locally stored in the radio-frequency amplifier so that there is no pulse DC current stress on the DC cables and connectors. In other words the amplifier can have its DC electrical ports power storage device either trickle charged continuously or charged when the magnetic resonance imaging system is not acquiring magnetic resonance data. This may reduce stresses on the DC cables because large pulses of power are not used and also it may reduce the stray magnetic field generated by the cables for supplying the DC electrical power.

In another embodiment each of the at least one radio-frequency amplifiers comprises at least one radio-frequency connector for connecting to one or more magnetic resonance imaging transmit coils. A magnetic resonance imaging transmit coil is a coil or antenna used to or operable to excite NMR or MRI resonances of a subject within the imaging zone. The radio-frequency amplifier housing may have additional connectors, for example additional coils. They may be for example receive coils, micro-coils on catheters, and other sensors. In some embodiments they may all be used simultaneously with a local transmitter receive coil connected to the radio-frequency amplifier.

In another embodiment the at least one radio-frequency amplifier comprises an RF combiner network for controlling a multi-element magnetic resonance imaging transmit coil. This for instance may be useful for doing techniques such as capital sense.

In another embodiment that at least one radio-frequency amplifier is a class D or a class E amplifier. These two types of amplifiers are particularly suited to functioning within a large magnetic field.

In another embodiment the at least one amplifier has a display operable for anyone of the following: displaying an operating status, indicating a safety status, and for controlling a service mode of the at least one amplifier.

In another embodiment the at least one radio-frequency amplifier is a transceiver. This may be beneficial because the radio-frequency amplifier may be used for acquiring magnetic resonance data in addition to exciting the nuclei within the imaging zone.

In another aspect the invention provides for a magnetic resonance imaging system comprising a subject support assembly according to an embodiment of the invention. The magnetic resonance imaging system comprises a magnet with an imaging zone. In some embodiments the DC power to the subject support may be supplied by a matched pair of DC cables which are positioned or arranged to reduce disturbance to the B0 field produced by the magnet.

In another embodiment the magnetic resonance imaging system comprises any one of the following: an interventional device, a catheter system, a biopsy needle system, a microwave ablation catheter system, a radio-frequency ablation catheter system, an ablation catheter system, a stent placement system, a radio-active seed placement system, a cryoablation system, a high-intensity focused ultrasound catheter system, a high-intensity focused ultrasound system, a chemoembolization system, an ECG system, and combinations thereof. This embodiment may be beneficial because with the amplifier mounted to the subject support it may be more convenient and have more space for adding an additional conventional type device or measurement system.

In another embodiment the subject support is operable for detachably receiving the at least one radio-frequency amplifier. The subject support comprises a first DC electrical connector. The at least one radio-frequency amplifier comprises a second DC electrical connector. The first DC electrical connector is operable for forming an electrical connection with the second DC electrical connector. The subject support is operable for supplying DC electrical power to the at least one radio-frequency amplifier when the first DC electrical connector is connected to the second DC electrical connector. The at least one radio-frequency amplifier comprises a DC electrical power storage device operable for powering the generation of the pulsed radio-frequency pulses by the at least one radio-frequency amplifier. The magnetic resonance imaging system further comprises a charging station operable for receiving the at least one radio-frequency generator. The charging station is operable for charging the DC electrical power storage device of a particular radio-frequency amplifier. For example when an amplifier is removed from the subject support it may be put on the charging station. In some embodiments the charging station may not only just charge the DC electrical power storage device but it may also be used to test the functioning of the radio-frequency amplifier or even install new software or firmware upgrades into the at least one radio-frequency amplifier.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
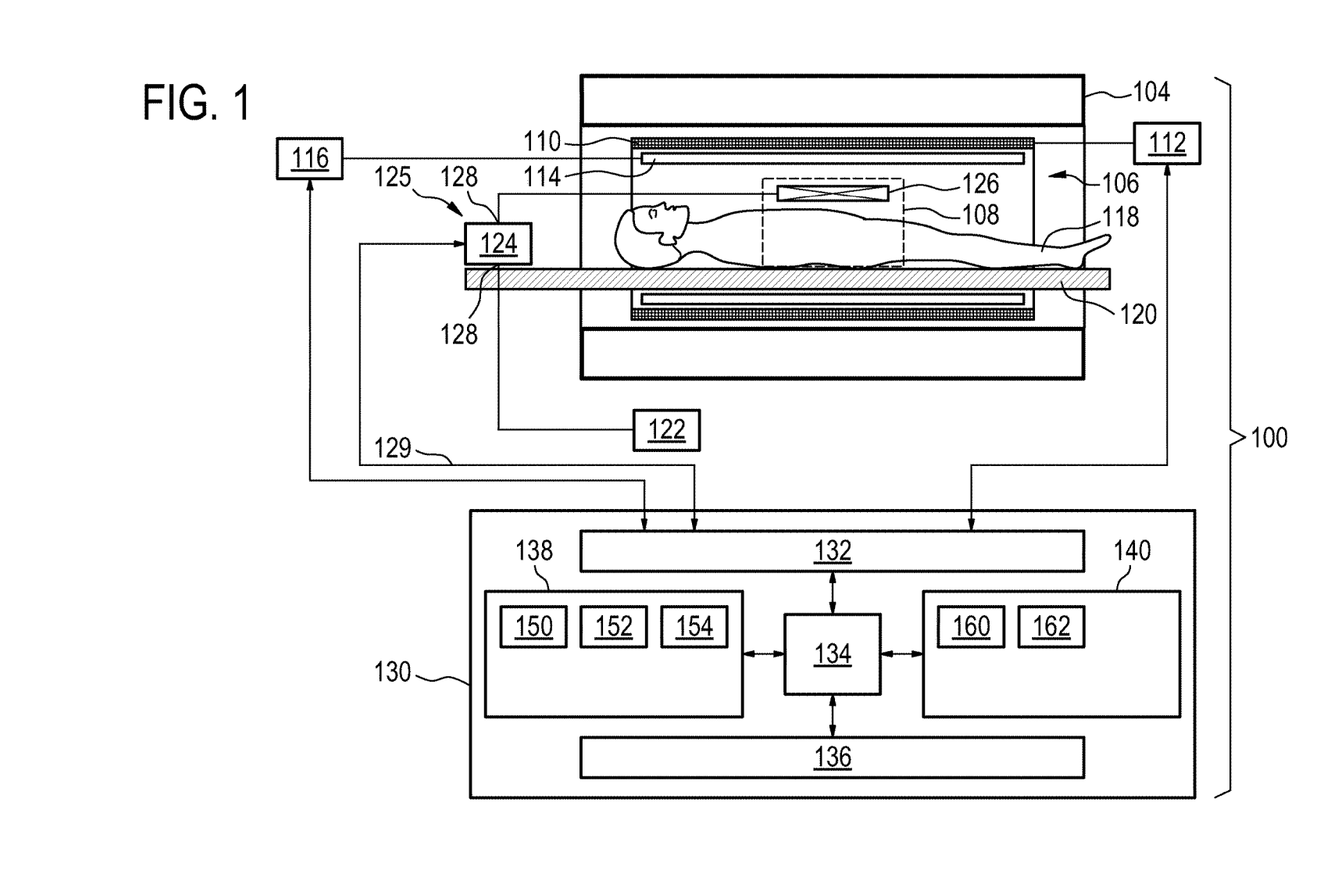
FIG. 1 illustrates an example of a magnetic resonance imaging system.

FIG. 1 shows an example a magnetic resonance imaging system 100. The magnetic resonance imaging system 100 comprises a magnet 104. The magnet 104 is a superconducting cylindrical type magnet 104 with a bore 106 through it. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 106 of the cylindrical magnet 104 there is an imaging zone 108 where the magnetic field is strong and uniform enough to perform magnetic resonance imaging.

Within the bore 106 of the magnet there is also a set of magnetic field gradient coils 110 which is used for acquisition of magnetic resonance data to spatially encode magnetic spins within the imaging zone 108 of the magnet 104. The magnetic field gradient coils 110 connected to a magnetic field gradient coil power supply 112. The magnetic field gradient coils 110 are intended to be representative. Typically magnetic field gradient coils 110 contain three separate sets of coils for spatially encoding in three orthogonal spatial directions. A magnetic field gradient power supply supplies current to the magnetic field gradient coils. The current supplied to the magnetic field gradient coils 110 is controlled as a function of time and may be ramped or pulsed.

Within the bore 106 of the magnet 104 is a body coil 114. The body coil 114 is shown as being connected to a receiver 116. In some embodiments body coil 114 may also be connected to a whole body coil radio frequency amplifier, however this is not shown in this example. If both a transmitter and a receiver 116 are connected to the whole body coil 114, a means for switching between the transmit and receive mode may be provided. For example a circuit with a pin diode may be used to select the transmit or receive mode.

On an end of the subject support 120 outside of the imaging zone 108 there is a radio-frequency amplifier 124 for local transmit and/or receive coils. A DC power supply 122 supplies DC power through the subject support 1280 to the radio frequency amplifier 124. The radio frequency amplifier is connected to a transmit coil 126. The transmit coil is smaller than the whole body coil and is placed near to the subject. The transmit coil 126 is shown as being positioned within the imaging zone 108 adjacent to the subject 118. Typically the whole body coil radio frequency amplifier will be located close or near to the magnet 104 and typically has a higher power than the radio frequency amplifier 124.

The transmit coil 126 is a radio-frequency coil for manipulating the orientations of magnetic spins within the imaging zone 108 and for receiving radio transmissions from spins also within the imaging zone 108. The radio frequency antenna may contain multiple coil elements. The radio frequency antenna may also be referred to as a channel or antenna. The radio-frequency coil 126 is connected to the radio-frequency amplifier 124. The radio-frequency coil 126 and radio-frequency amplifier 124 may be replaced by integrated transmit and receive coils and a transceiver.

There is a connection 128 between an output of the radio-frequency amplifier 124 and the transmit coil 126. The magnetic field gradient coil power supply 112, the receiver 116, and the radio-frequency amplifier 124 are shown as being connected to a hardware interface 132 of a computer 130. There is a connection between the hardware interface 132 and the radio-frequency amplifier 124 that is labeled 129. In some embodiments 129 may be a fiber optic connection between the hardware interface 132 and the radio-frequency amplifier 124. In some embodiments the fiber optic 129 is also routed through the subject support 120.

The computer system 130 further comprises a processor 134. The processor 134 is connected to the hardware interface 132, a user interface 136, computer storage 138, and computer memory 140. The computer storage 138 is shown as containing a pulse sequence 150. The pulse sequence is a series of commands or information which may be used to generate commands for controlling the operation of the magnetic resonance imaging system 100 to acquire magnetic resonance data. The computer storage is also shown as containing magnetic resonance data 152 that was acquired using the pulse sequence 150. The computer storage 138 is also shown as containing a magnetic resonance image 154 that was reconstructed from the magnetic resonance data 152.

The computer memory 140 is shown as containing a control module 160. The control module 160 contains computer-executable code which enables the processor 134 to control the operation and function of the magnetic resonance imaging system 100. This includes using the pulse sequence 150 to acquire the magnetic resonance data 152. The computer memory 140 is further shown as containing an image reconstruction module 162. The image reconstruction module contains computer-executable code which enables the processor 134 to perform mathematical functions on the magnetic resonance data 152 to reconstruct the magnetic resonance image 154.

In some examples the receiver 116 and the transceiver 124 are incorporated into a single unit, in this case the receiver 116 would be incorporated into the RF generator 124. In some embodiments the transmit coil 126 is also a transmit and receive coil. In some embodiments the body coil 114 may also be connected to the amplifier 124, and the radio-frequency coil 126 may also be used as a receive coil. This could for instance be accomplished by using a local PIN diode switch to change between a transmit and a receive mode.

In some embodiments the transmit coil 126 has multiple coil elements. In this case the radio-frequency amplifier 124 may have multiple outputs for connecting to each element of the coil 126. The amplifier 124 may also be operable for controlling the amplitude and phase of radio-frequency supplied to each of these coil elements.

Figure 2:
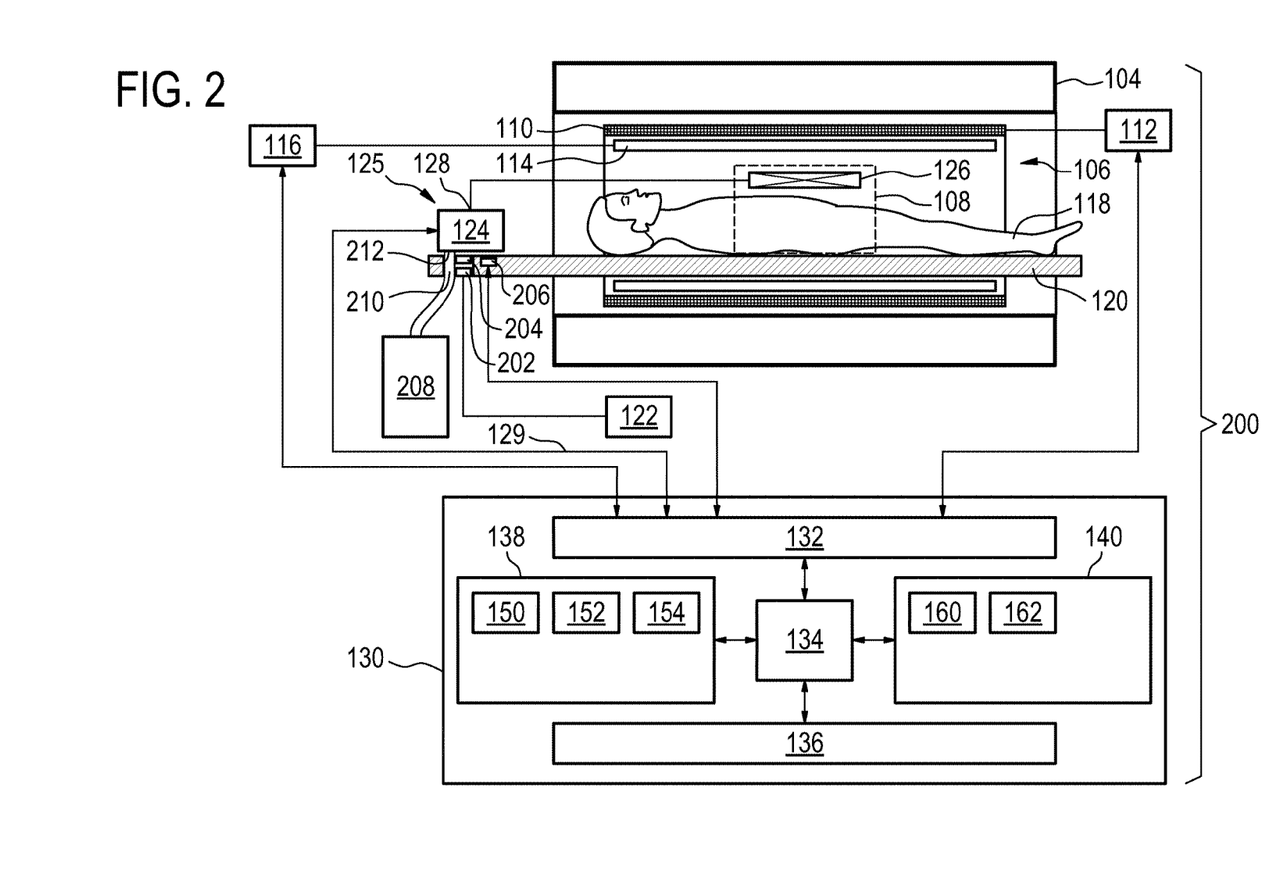
FIG. 2 illustrates a further example of a magnetic resonance imaging system.

FIG. 2 shows a magnetic resonance imaging system 200 similar to that shown in FIG. 1. There are however additional features incorporated into the subject support 120. Within the subject support 120 there is a first DC electrical connector 202 connected to the DC supply 122. There is a second DC electrical connector 204 connected to the radio-frequency amplifier 124. These connectors enable the radio-frequency amplifier 124 to receive DC electrical power from the DC supply 122. There is also shown a sensor 206 embedded in the subject support 120. The sensor 206 is able to detect if there is a radio-frequency generator 124 mounted there or not. The connectors 202, 204 enable the radio-frequency amplifier 124 to be easily removed or added.

In some examples there may be multiple connectors which enable the radio-frequency amplifier 124 to be placed in different positions or even multiple amplifiers to be used at a single time. The sensor 206 has a connection to the hardware interface 132 which enables the control module 160 to determine if there is the radio-frequency amplifier 124 there or not. In some embodiments the computer system 130 would also control the supply of DC electrical power 122 to deactivate DC electrical power when there is not a radio-frequency amplifier 124 mounted there. In other embodiments the sensor 206 may even be connected directly to the DC supply 122. A controller within the DC supply 122 would then enable or disable the supply of electrical power to the position where the radio-frequency amplifier 124 is mounted.

Also shown is a chiller 208. The chiller is connected to the subject support 120 via a first coolant connector 210. The radio-frequency amplifier 124 has a second coolant connector 212 that mates with the first coolant connector 210 and enables the chiller 208 to chill the radio-frequency amplifier with coolant. Not shown in this diagram but the connection 129 used to control the operation of the radio-frequency amplifier 124 may also be via a connector within the subject support 120.

Figure 3:
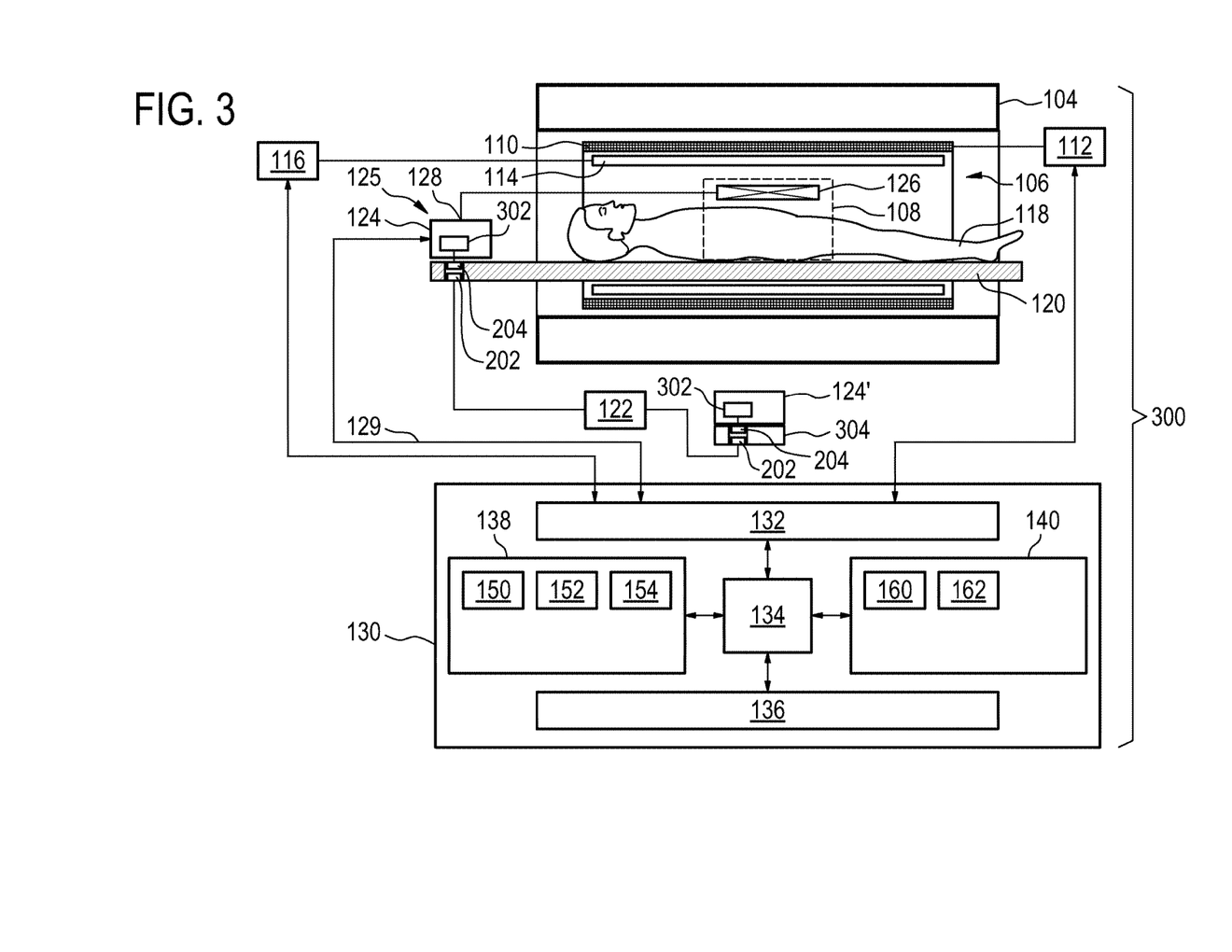
FIG. 3 illustrates a further example of a magnetic resonance imaging system.

FIG. 3 shows an example of a magnetic resonance imaging system 300 that is similar to that shown in FIGS. 2 and 3. In this example again are shown the connectors 202 and 204 within the subject support 120. However, in this embodiment there is a DC electrical storage device 302 which is charged by the DC supply 122. This may be particularly beneficial when the radio-frequency power supplied to the transmit coil 126 is supplied in a pulsed manner. Using the DC electrical storage device 302 does not require a pulse of DC power to operate the radio-frequency generator 124. This arrangement may be operated such that the DC electrical storage device 302 is trickle charged. In some embodiments the DC power may also be shut off during the acquisition of magnetic resonance data. In this example there is also shown a charging station 304.

The charging station 304 is connected to the DC supply 122 and has an additional radio-frequency generator 124' that is identical to the generator 124. This may be beneficial because the radio-frequency generator 124' may have a full charge when it is installed into the subject support 120. The charging station 304 may have additional functions in some instances. For instance there may be a fiber optic connection which enables the radio-frequency generator 124' to be controlled and tested. For instance the charging station 304 may have dummy loads that the radio-frequency generator 124' can be connected to. The charging station 304 may also be adapted such that it can supply new software or firmware to the radio-frequency generator 124' also. In such embodiments it may be that the hardware interface 132 is connected to the charging station 304 and/or the DC power supply 122.

Figure 4:
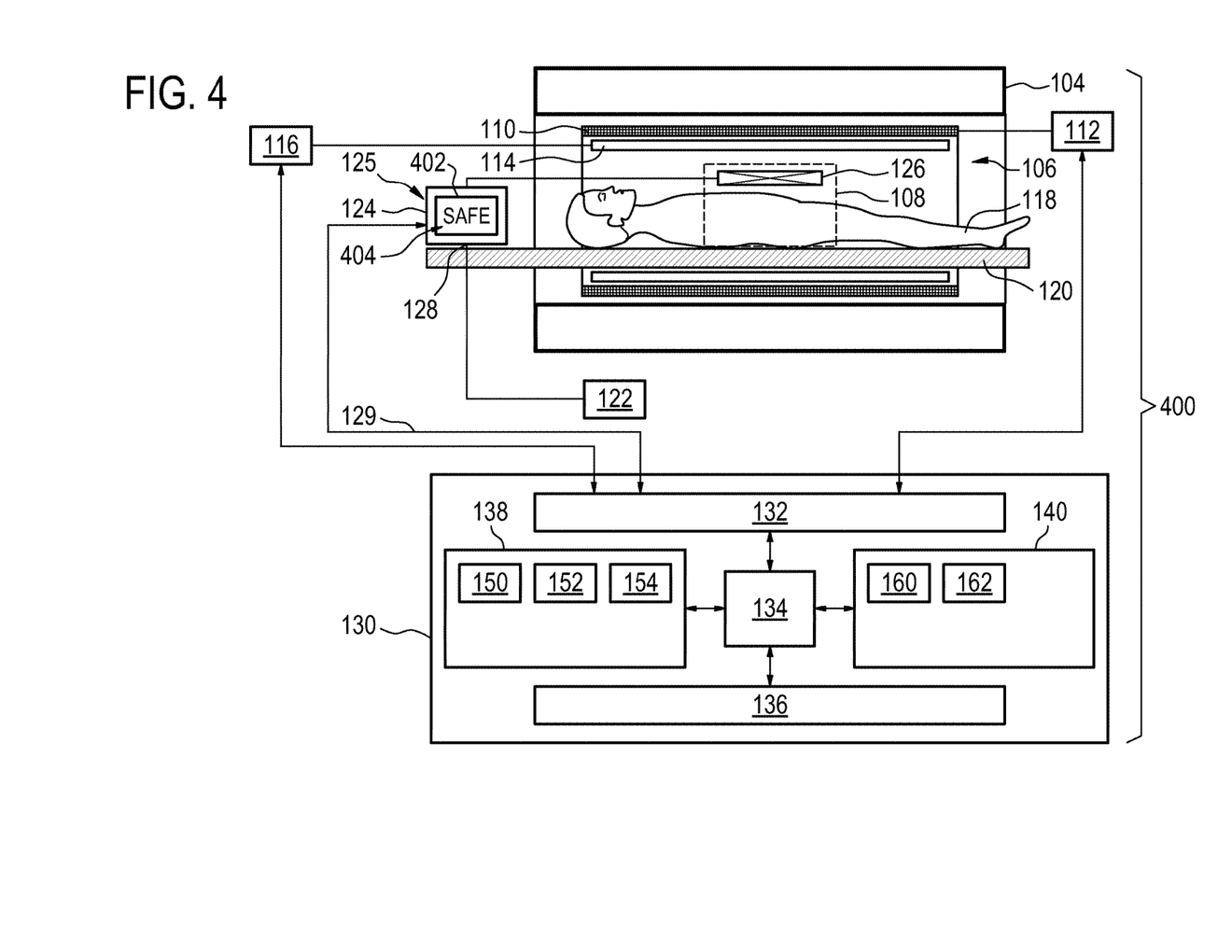
FIG. 4 illustrates a further example of a magnetic resonance imaging system.

FIG. 4 shows a further example of a magnetic resonance imaging system that is similar to that shown in FIG. 1. However, in this case the radio-frequency generator 124 has a display 402. On the display there is printed a message 404. The message 404 may for instance be used to display a safety message or an operating condition. In other embodiments the display 402 may incorporate or be replaced by a touch screen or other user interface. This may enable service personnel to enter into a service mode of the radio-frequency generator 124.

Figure 5:
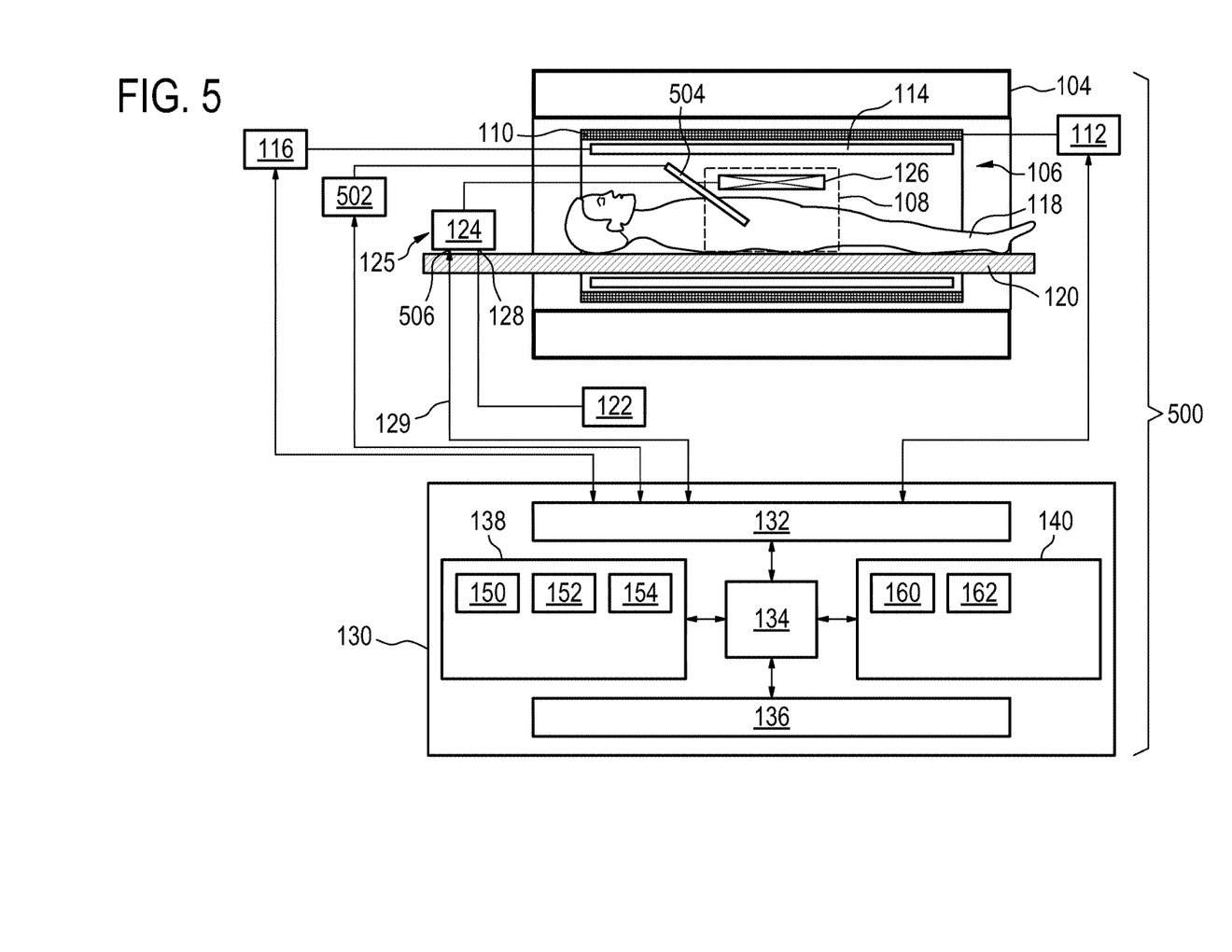
FIG. 5 illustrates a further example of a magnetic resonance imaging system.

FIG. 5 shows a magnetic resonance imaging system 500 similar to that shown in FIG. 1. However, additionally in this system there is an interventional device 502 which is connected to the hardware interface 132. The interventional device is connected to a catheter 504 that is inserted into the subject 118. The processor 134 is able to control the interventional device 502 using code in the control module 160. The interventional device 502 and the catheter 504 are intended to be representative. They may be a variety of any sorts of devices or sensors additionally used on the subject 118. For instance they may be, but are not limited to: an interventional device, a catheter system, a biopsy needle system, a microwave ablation catheter system, a radio-frequency ablation catheter system, an ablation catheter system, a stent placement system, a radio-active seed placement system, a cryoablation system, a high-intensity focused ultrasound catheter system, a high-intensity focused ultrasound system, a chemoembolization system, an ECG system. In this embodiment there is also shown that there is a connection 506 through the subject support 120 or the fiber optic 129 to the radio-frequency amplifier 124. For instance there may be connectors in the subject support 120 and a mating connector in the radio-frequency amplifier 124.

The magnets of conventional tunnel-shaped Magnetic Resonance (MR) systems exhibit several severe limitations when addressing issues like larger bore size or higher field strength. Increasing the bore size by scaling the MR system results in massively increasing component cost, ineffective body coils and the need for extremely large RF-power especially for multi-transmit systems.

Examples described herein may be operable to drive the surface Tx/Rx coil array with RF amplifiers inserted in patient table. The RF chain may benefit from this modular and scalable approach, which reduces cost and increases performance. The optimal position is in the table in order to guarantee the proximity to the TR array and minimize the power losses.

The amplifier embedded in the table is easy to access for service.

RF coils are a means for signal excitation and reception in magnetic resonance imaging. MRI systems with large bores typically suffer from low B1-levels due to system constraints (cost, available RF-power, . . . ) and poor system body coil performance. For a lot of clinical advanced applications, high local B1 is required for RF shimming, diffusion weighted experiments, inflow suppression etc.

The examples describe herein may use Transmit/Receive (Tx/Rx) transmit arrays are used to produce RF fields and the amplifiers needed to drive the coils are hidden in the table. Ideally one amplifier per Tx channel is needed.

Examples described herein may overcome the following problems or disadvantages:
- power losses due to long cable between amplifier and Tx coil,
- control of relevant RF parameters in the interface (i.e. high impedance),
- complexity in cabling and connection to Tx/Rx coil,
- it make the Tx/Rx coil an independent unit within the table,
- each amplifier can be FRU, easily accessible for service, and
- when needed, cooling can be introduced in the patient table Examples described herein may drive a surface Tx/Rx coil array an RF amplifiers inserted in patient table. Embedding the amplifier in the table gives several possibilities:
- modular and scalable approach: possibility of adding more modules when needed (cost and performances),
- proximity to Tx/Rx coil: control of RF properties and losses,
- possibility of cooling the RF amplifier within the table, and
- easy to access for service.

Figure 6:
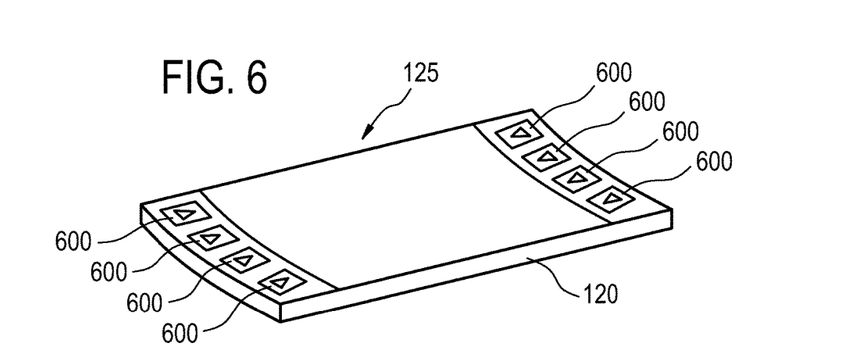
FIG. 6 illustrates an example of a subject support assembly.

FIG. 6 shows an example of a subject support assembly 125. The subject support assembly comprises a subject support 120 and a number of connectors 600. Connectors for instance may have a cover which slides closed to protect any DC electrical connectors and/or fiber optic connectors and/or coolant system connectors. Having multiple connectors 600 may enable more than one radio-frequency generator 124 to be placed and mounted onto the subject support assembly 125. In some embodiments everything is supplied in one connector 600. In other embodiments there is a particular polarity supplied in each of the connectors 600.

FIG. 6 shows an artistic impression of amplifiers in the table. Examples of individual amplifiers located at both ends of the patient bed. Here the amplifiers are integrated in pockets or recess openings. Supply, cooling and control is rooted and integrated in the patient bed.

Figure 7:
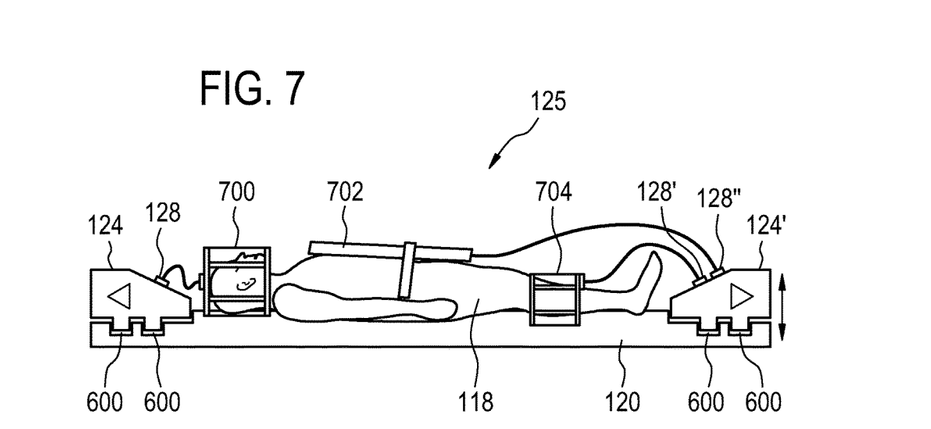
FIG. 7 illustrates a further example of a subject support assembly.

FIG. 7 shows the subject support assembly 125 again. There is the subject support 120 and a subject 118 reposing on the subject support 120. There is a first radio-frequency generator 124 mounted near the head of the subject and a second radio-frequency generator 124' mounted near the feet of the subject 118. When inserted into a magnetic resonance imaging system the amplifiers will be away from the imaging zone. The radio-frequency generators 124 and 124' are shown as being removable. The two generators 124, 124' have plugs which are made into the connectors 600. The first radio-frequency generator 124 has a first section between the amplifier and coil 128. This enables a connection to a head transmission coil 700.

The second radio-frequency amplifier 124' has a second connection 128' and a third connection 128". The first connection 128' is connected to a knee transmission coil 704 and the third connection 128" is connected to a surface anterior transmission coil 702. FIG. 7 illustrates how depending upon the desired measurements in the magnetic resonance imaging system, the radio-frequency system can be configured differently. For instance if only measurements on the subject's 118 head are desired then the radio-frequency amplifier 124' and the associated coils 702, 704 may be removed.

FIG. 7 sows several RF amplifiers 124, 124' located in a patient table 120. The RF amplifier adapter can contain the RF amplifier and/or the monitor and signal conditioning of the RF amplifier (in case the amplifier is embedded in the table). Individual local transmit and receive coils such as knee 704, head 700 or body surface coils 702 are connected to the amplifier adapter. Due to the short cable connection, RF losses by the connecting cable are negligible.

Figure 8:
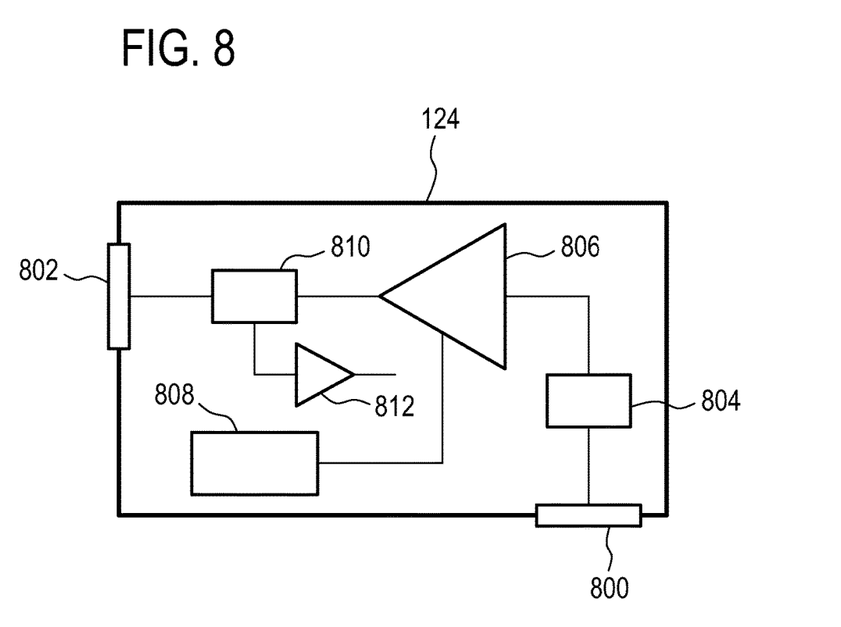
FIG. 8 illustrates an example of a radio-frequency amplifier.

FIG. 8 shows one possible example of a radio-frequency amplifier 124. There is an interface connection 800 which may be used to connect two connectors on the subject support. This may also include connections for the fiber optic control, the DC power, and/or the coolant. In this example the connector 800 is shown as being connected to a Direct Digital Synthesizer (DDS) 804. The individual complex RF pulses generated by the DDS are controlled in amplitude, phase and frequency. In some examples a multi channel transmit array is connected to multiple coil elements. In this example each RF amplifier may be operable to generate its individual transmit signal. The digital input signal for the DDS may in some examples be delivered via an optical connection to the computer.

The DDS 804 is connected to an RF amplifier 806. The RF amplifier 806 is controlled by a digital control, supply and driver 808. The output of the RF amplifier 806 is connected to a send and receive switch 810. The send and receive switch 810 is also connected to the interface connector to the coil array 802 and to a preamplifier 812 which is connected to an analogue-to-digital converter. The switch 810 connects either the output of the radio-frequency amplifier to the connector 802 or connects the connector 802 to the input of the preamplifier 812. In this way the radio-frequency generator 124 is configured for both sending and receiving a signal. This for instance could be connected to a transmit and receive coil.

FIG. 8 One possible embodiment of an adapter housing with integrated RF amplifiers. There is only one RF chain is shown, although in a more complicated design multiple RF chains could be present. The adapter has an interface connection 800 to the patient bed for supply and control signals. The control signals are transmitted optically via connector, which makes signal connection obsolete. MR transmit pulses are generated locally via a DDS 804 housed in RF amp adapter. Additional cooling of local amplifiers is performed via interface connection (water, forced air cooling). With the advent of efficient switch mode class D/E MR RF amplifiers, cooling of the RF modules is achievable.

The features of the various examples shown in FIGS. 1 to 8 may be combined.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 magnetic resonance imaging system
104 magnet
106 bore of magnet
108 imaging zone
110 magnetic field gradient coils
112 magnetic field gradient coil power supply
114 body coil
116 receiver
118 subject
120 subject support
122 DC supply
124 radio frequency amplifier
124' radio frequency amplifier
125 subject support assembly
126 transmit coil
128 connection between amplifier and coil
128' connection between amplifier and coil
128" connection between amplifier and coil
129 fiber optic
130 computer system
132 hardware interface
134 processor
136 user interface
138 computer storage
140 computer memory
150 pulse sequence
152 magnetic resonance data
154 magnetic resonance image
160 control module
162 image reconstruction module
200 magnetic resonance imaging system
202 first DC electrical connector
204 second DC electrical connector
206 sensor
208 chiller
210 first coolant connector
212 second coolant connector
300 magnetic resonance imaging system
302 DC electrical storage device
304 charging station
400 magnetic resonance imaging system
402 display
404 message
500 magnetic resonance imaging system
502 interventional device
504 catheter
506 connection
125 subject support assembly
600 connectors
700 head transmission coil 702 surface anterior transmission coil
704 knee transmission coil
800 interface connection to bed
802 interface connection to coil array
804 DDS
806 RF amplifier
808 digital control, supply and driver
810 send/receive switch
812 pre-amplifier to AD converter

The invention claimed is:

1. A subject support assembly for a magnetic resonance imaging system, comprising: a radio frequency transmit coil and a subject support for supporting a subject within an imaging zone of a magnet of the magnetic resonance imaging system, wherein the subject support assembly supports at least one radio frequency amplifier for driving the radio frequency transmit coil and positioned outside of the imaging zone when the subject support is in use in the magnetic resonance imaging system, and wherein the subject support assembly is provided with a DC power source for supplying DC electrical power to the at least one radio frequency amplifier, wherein the at least one radio frequency amplifier is detachably supported by the subject support, wherein the subject support comprises a first DC electrical connector, wherein the at least one radio frequency amplifier comprises a second DC electrical connector, wherein the first DC electrical connector is operable for forming an electrical connection with the second DC electrical connector, and wherein the subject support is operable for supplying DC electrical power to the at least one radio frequency amplifier when the first DC electrical connector is connected to the second DC electrical connector.

2. The subject support assembly of claim 1, wherein the subject support comprises a first coolant connector, wherein the at least one radio frequency amplifier comprises a second coolant connector, wherein the first coolant connector is operable for forming a connection with the second coolant connector, wherein the subject support is operable to supply coolant to the at least one radio frequency amplifier when the first coolant connector is connected with the second coolant connector.

3. The subject support assembly of claim 1, wherein the subject support comprises a sensor operable for determining if the at least one radio frequency generator is connected to the subject support.

4. The subject support assembly of claim 1, wherein the subject support comprises a first fiber optic connector, wherein the at least one radio frequency amplifier comprises a second fiber optic connector, wherein the first fiber optic connector is operable for forming a connection with the second fiber optic connector, wherein the subject support is any one of the following: operable to transmit radio frequency control signals to the at least one radio frequency amplifier, receive data from the at least one radio frequency amplifier, and combinations thereof.

5. The subject support assembly of claim 1, wherein the subject support comprises the at least one radio frequency amplifier.

6. The subject support assembly of claim 1, wherein the at least one radio frequency amplifier is incorporated into the subject support.

7. The subject support assembly of claim 5, wherein the at least one radio frequency amplifier comprises a DC electrical power storage device operable for powering the generation of pulsed radio-frequency pulses by the at least one radio frequency amplifier.

8. The subject support assembly of claim 5, wherein each of the at least one radio frequency amplifier comprises at least one radio frequency connector for connecting to one or more magnetic resonance imaging transmit coils.

9. The subject support assembly of claim 5, wherein the at least one radio frequency amplifier comprises a RF combiner network for controlling a multi-element magnetic resonance imaging transmit coil.

10. The subject support assembly of claim 5, wherein the at least one radio frequency amplifier is a class D or class E amplifier.

11. The subject support assembly of claim 5, wherein the at least one amplifier has a display operable for any one of the following: displaying an operating status, indicating a safety status, and for controlling a service mode of the at least one amplifier.

12. A magnetic resonance imaging system comprising:
a magnet with an imaging zone; and
a subject support assembly including: a radio frequency transmit coil and a subject support for supporting a subject within the imaging zone, wherein the subject support assembly supports at least one radio frequency amplifier for driving the radio frequency transmit coil and positioned outside of the imaging zone when the subject support is in use in the magnetic resonance imaging system, and wherein the subject support assembly is provided with a DC power source for supplying DC electrical power to the at least one radio frequency amplifier, wherein the at least one radio frequency amplifier is detachably supported by the subject support, wherein the subject support comprises a first DC electrical connector, wherein the at least one radio frequency amplifier comprises a second DC electrical connector, wherein the first DC electrical connector is operable for forming an electrical connection with the second DC electrical connector, and wherein the subject support is operable for supplying DC electrical power to the at least one radio frequency amplifier when the first DC electrical connector is connected to the second DC electrical connector.

13. The magnetic resonance imaging system of claim 12, wherein the magnetic resonance imaging system comprises at least one selected from a group consisting of: an interventional device, a catheter system, a biopsy needle system, a microwave ablation catheter system, a radio-frequency ablation catheter system, an ablation catheter system, a stent placement system, a radio-active seed placement system, a cryoablation system, a high intensity focused ultrasound catheter system, a high intensity focused ultrasound system, a chemoembolization system, a ECG system, and combinations thereof.

14. The magnetic resonance imaging system of claim 12, wherein the subject support is operable for detachably receiving the at least one radio frequency amplifier, wherein the subject support comprises a first DC electrical connector, wherein the at least one radio frequency amplifier comprises a second DC electrical connector, wherein the first DC electrical connector is operable for forming an electrical connection with the second DC electrical connector, and wherein the subject support is operable for supplying DC electrical power to the at least one radio frequency amplifier when the first DC electrical connector is connected to the second DC electrical connector, wherein the at least one radio frequency amplifier comprises a DC electrical power storage device operable for powering the generation of pulsed radio-frequency pulses by the at least one radio frequency amplifier, wherein the magnetic resonance imaging system further comprises a charging station operable for receiving the at least one radio frequency generator, and wherein the charging station is operable for charging the DC electrical power storage device.

15. The magnetic resonance imaging system of claim 14, wherein the subject support assembly comprises a sensor operable for determining if the at least one radio frequency generator is connected to the subject support.

16. The magnetic resonance imaging system of claim 12, wherein the subject support comprises a first fiber optic connector, wherein the at least one radio frequency amplifier comprises a second fiber optic connector, wherein the first fiber optic connector is operable for forming a connection with the second fiber optic connector, wherein the subject support is any one of the following: operable to transmit radio frequency control signals to the at least one radio frequency amplifier, receive data from the at least one radio frequency amplifier, and combinations thereof.

17. The magnetic resonance imaging system of claim 12, wherein the at least one radio frequency amplifier is incorporated into the subject support.

18. The magnetic resonance imaging system of claim 17, wherein the at least one radio frequency amplifier comprises a DC electrical power storage device operable for powering the generation of pulsed radio-frequency pulses by the at least one radio frequency amplifier.

19. The magnetic resonance imaging system of claim 17, wherein the at least one radio frequency amplifier comprises a RF combiner network for controlling a multi-element magnetic resonance imaging transmit coil.

20. The magnetic resonance imaging system of claim 17, wherein the at least one radio frequency amplifier has a display operable for any one of the following: displaying an operating status, indicating a safety status, and for controlling a service mode of the at least one radio frequency amplifier.

* * * * *